(12) United States Patent
Shenkal et al.

(10) Patent No.: US 11,134,719 B2
(45) Date of Patent: *Oct. 5, 2021

(54) E-CIGARETTE WITH VALVE ALLOWING EXHALE FILTER

(71) Applicant: Philter Labs, Inc., San Diego, CA (US)

(72) Inventors: Yuval Shenkal, Cardiff, CA (US); John Grimm, Santee, CA (US)

(73) Assignee: Philter Labs, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/847,564

(22) Filed: Apr. 13, 2020

(65) Prior Publication Data

US 2020/0305507 A1    Oct. 1, 2020

Related U.S. Application Data

(63) Continuation of application No. 15/070,186, filed on Mar. 15, 2016, now Pat. No. 10,617,148, which is a
(Continued)

(51) Int. Cl.
*A24F 40/485*    (2020.01)
*A61M 15/06*    (2006.01)
(Continued)

(52) U.S. Cl.
CPC .............. *A24F 40/485* (2020.01); *A24D 3/17* (2020.01); *A24F 13/00* (2013.01); *A24F 40/50* (2020.01);
(Continued)

(58) Field of Classification Search
CPC ...... A24F 47/008; A24F 40/485; A61M 15/06
See application file for complete search history.

(56) References Cited

U.S. PATENT DOCUMENTS

| | | |
|---|---|---|
| 3,731,678 A | 5/1973 | Pyzel |
| 4,899,766 A | 2/1990 | Ross |

(Continued)

FOREIGN PATENT DOCUMENTS

| | | | | |
|---|---|---|---|---|
| CA | 2121282 C | * | 4/1997 | ............. A24F 13/00 |
| CA | 2252198 | | 5/2000 | |

(Continued)

OTHER PUBLICATIONS

English abstract CN10578233A, dated 2016 (Year: 2016).*
English Abstract CN20432277U, dated 2015 (Year: 2015).*
English abstcatCN105011379A, dated 2015 (Year: 2015).*

*Primary Examiner* — Anthony Calandra
(74) *Attorney, Agent, or Firm* — Sheppard, Mullin, Richter & Hampton LLP

(57) ABSTRACT

An electronic cigarette particularly adaptable to vaporize liquid material also having exhale filter function is disclosed herein. The exhale function is useful to prevent second hand smoke in an enclosed environment, for example. An innovative diverter valve assembly comprises a unique duckbill valve configuration diverting air through a cooker chamber and into a mouthpiece in an inhale function and diverting exhaled air around the cooker chamber in the exhale function and through a filter assembly. A preferred embodiment further introduces a unique shape to the smoking instrument being elliptical in the cross-section and tapering to proximal and distal ends.

25 Claims, 11 Drawing Sheets

Related U.S. Application Data continuation of application No. 14/121,917, filed on Nov. 3, 2014, now Pat. No. 9,402,422.

(60) Provisional application No. 62/133,414, filed on Mar. 15, 2015, provisional application No. 61/899,070, filed on Nov. 1, 2013.

(51) Int. Cl.

| | |
|---|---|
| *A24D 3/17* | (2020.01) |
| *A24F 13/00* | (2006.01) |
| *B01D 46/52* | (2006.01) |
| *B01D 46/00* | (2006.01) |
| *B01D 46/30* | (2006.01) |
| *B01D 46/10* | (2006.01) |
| *F16K 15/14* | (2006.01) |
| *H05B 3/40* | (2006.01) |
| *A61M 11/04* | (2006.01) |
| *A24F 40/50* | (2020.01) |
| *A24F 40/60* | (2020.01) |
| *A24F 40/20* | (2020.01) |

(52) U.S. Cl.
CPC ........... *A24F 40/60* (2020.01); *A61M 11/042* (2014.02); *A61M 15/06* (2013.01); *B01D 46/0017* (2013.01); *B01D 46/0026* (2013.01); *B01D 46/0041* (2013.01); *B01D 46/0097* (2013.01); *B01D 46/10* (2013.01); *B01D 46/30* (2013.01); *B01D 46/52* (2013.01); *F16K 15/147* (2013.01); *H05B 3/40* (2013.01); *A24F 40/20* (2020.01); *A61M 2205/3653* (2013.01); *A61M 2205/584* (2013.01); *A61M 2205/75* (2013.01); *A61M 2205/8206* (2013.01)

(56) References Cited

U.S. PATENT DOCUMENTS

| | | | |
|---|---|---|---|
| 5,160,518 A | 11/1992 | Vega, Jr. | |
| 5,353,814 A | 10/1994 | Martin | |
| 5,388,595 A | 2/1995 | Shafer | |
| 5,396,907 A | 3/1995 | Rojas Henao et al. | |
| 5,495,859 A | 3/1996 | Bowen et al. | |
| 5,529,078 A | 6/1996 | Rehder | |
| 5,575,279 A | 11/1996 | Beplate | |
| 5,666,978 A | 9/1997 | Counts et al. | |
| 5,814,118 A | 9/1998 | Wickland et al. | |
| 5,964,909 A | 10/1999 | Brunner | |
| 6,104,032 A * | 8/2000 | Means | B01D 46/0086 250/341.7 |
| 6,761,169 B2 | 7/2004 | Eswarappa | |
| 9,167,849 B2 | 10/2015 | Adamic | |
| 9,380,813 B2 | 7/2016 | McCullough | |
| 10,028,528 B2 | 7/2018 | Pero | |
| 10,588,344 B2 | 3/2020 | Shenkal | |
| 10,786,001 B2 | 9/2020 | Prog | |
| 2006/0107965 A1 | 5/2006 | Marshall | |
| 2007/0225631 A1 | 9/2007 | Bowlin | |
| 2008/0060664 A1 | 3/2008 | Richards | |
| 2008/0149118 A1 | 6/2008 | Oglesby et al. | |
| 2008/0230052 A1 | 9/2008 | Montaser | |
| 2010/0291058 A1 | 11/2010 | Bowlin | |
| 2011/0073120 A1 | 3/2011 | Adamic | |
| 2011/0277757 A1 | 11/2011 | Terry et al. | |
| 2012/0325227 A1 | 12/2012 | Robinson | |
| 2013/0255702 A1 | 10/2013 | Griffith | |
| 2014/0123990 A1 | 5/2014 | Timmermans | |
| 2014/0190496 A1 | 7/2014 | Wensley et al. | |
| 2015/0150305 A1 | 6/2015 | Shenkal | |
| 2015/0216236 A1 | 8/2015 | Bless et al. | |
| 2015/0342259 A1 | 12/2015 | Baker | |
| 2016/0219932 A1 | 8/2016 | Glaser | |
| 2016/0270446 A1 | 9/2016 | Shenkal | |
| 2017/0049976 A1 | 2/2017 | Reed | |
| 2017/0245545 A1 | 8/2017 | Johnson, III et al. | |
| 2018/0042291 A1 | 2/2018 | Richards | |
| 2019/0037923 A1 | 2/2019 | Shenkal | |
| 2019/0150516 A1 | 5/2019 | Shenkal | |
| 2019/0307165 A1 | 10/2019 | Carney | |

FOREIGN PATENT DOCUMENTS

| | | | |
|---|---|---|---|
| CA | 2799312 A1 * | 10/2011 | ............ A24F 13/00 |
| CN | 1124914 | 6/1996 | |
| CN | 102946746 | 2/2013 | |
| CN | 204232277 | 4/2015 | |
| CN | 105011379 | 11/2015 | |
| CN | 105768233 | 7/2016 | |
| TW | 201112974 | 4/2011 | |

\* cited by examiner

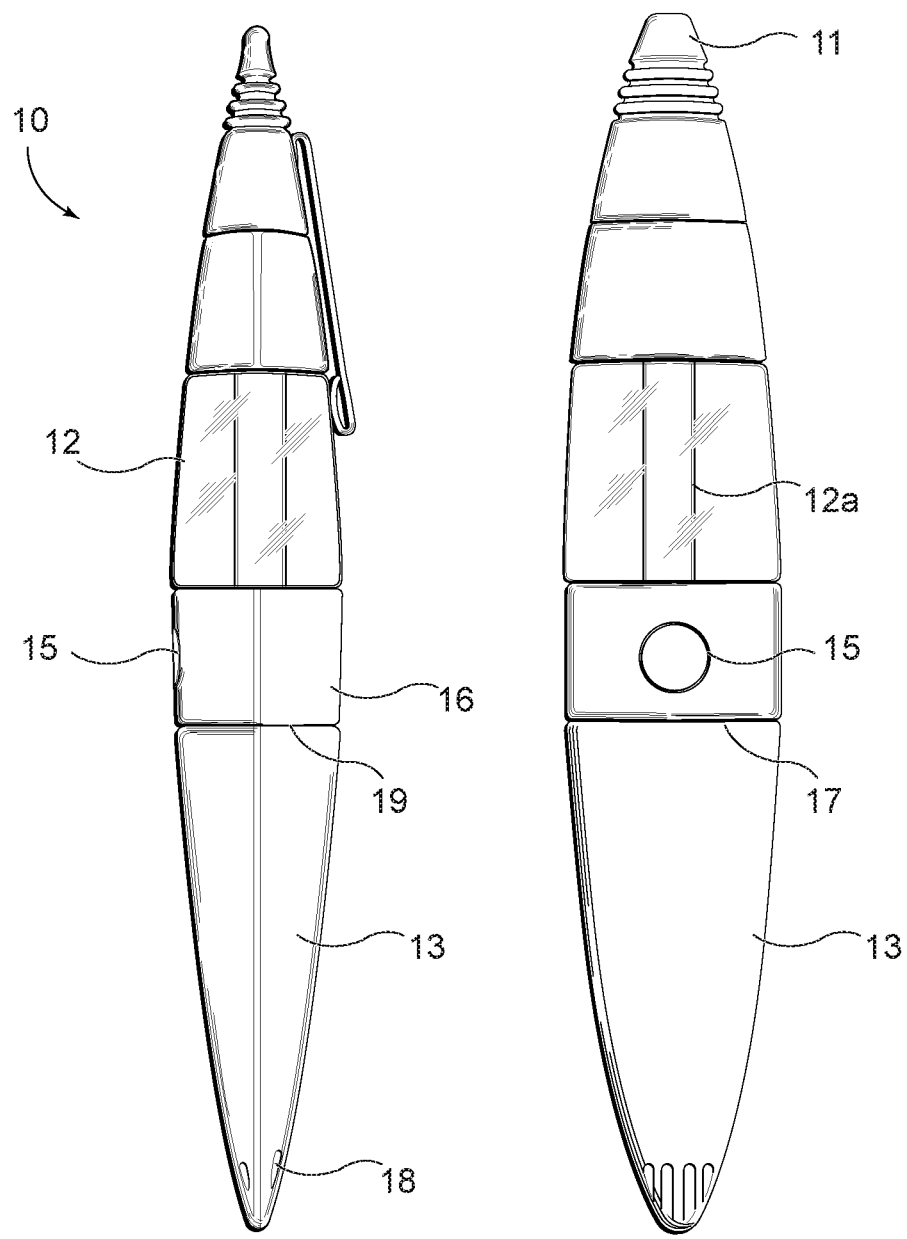
*FIG. 1B*  *FIG. 1C*

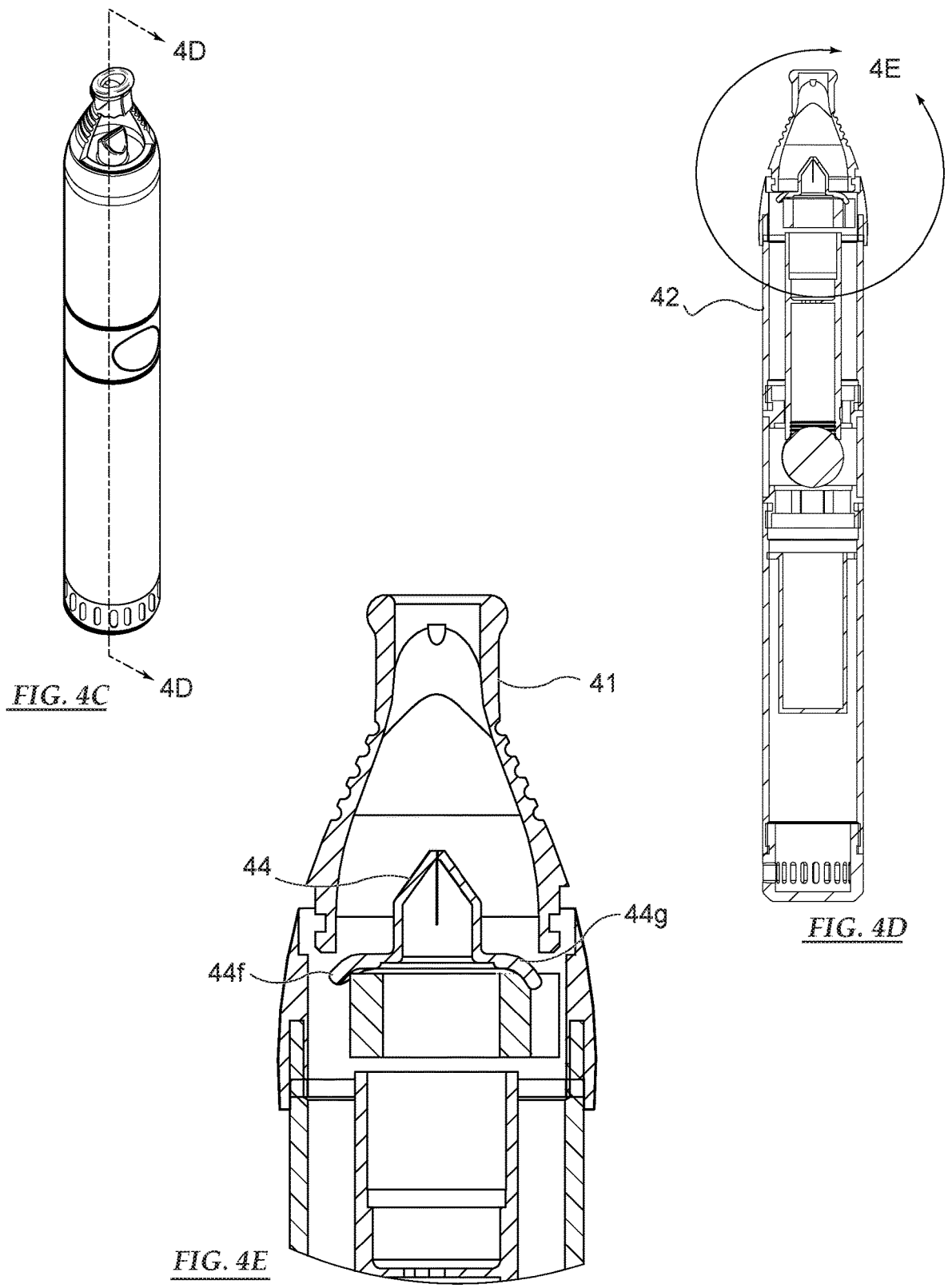

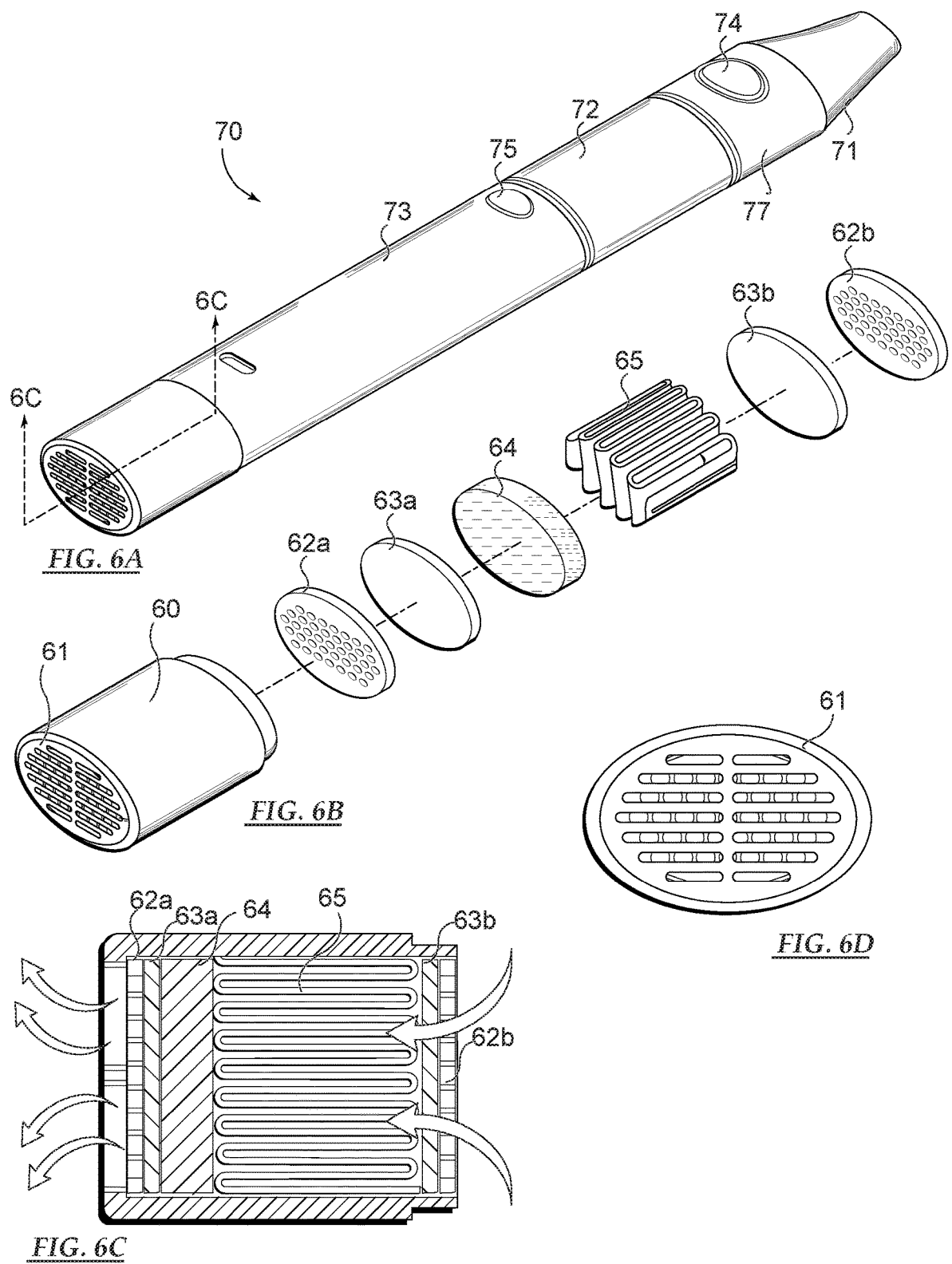

US 11,134,719 B2

E-CIGARETTE WITH VALVE ALLOWING EXHALE FILTER

CROSS-REFERENCE TO RELATED APPLICATIONS

This patent application is a continuation of and claims the benefit of U.S. patent application Ser. No. 15/070,186 filed on Mar. 15, 2016, which claims the benefit of U.S. Provisional Patent Application No. 62/133,414 filed on Mar. 15, 2015 and entitled "E-Cigarette with Valve Allowing Exhale Filter," and the benefit (as a continuation-in-part) of U.S. patent application Ser. No. 14/121,917 filed on Nov. 3, 2014 and entitled "Hybrid E-Cigarette/Vaporizer with Exhale Filter Capability," which in turn claims the benefit of U.S. Provisional Patent Application No. 61/899,070 filed on Nov. 1, 2013; accordingly, the entire contents of all of these patent applications are hereby expressly incorporated herein by reference.

BACKGROUND

Field of the Invention

The present invention pertains generally to electronic smoking devices. More specifically, the present invention relates to an electronic cigarette having a dual action valve to provide appropriate channeling of air in an inhale and an exhale function.

Description of the Prior Art

Smoking tobacco or other plant material has notoriously been practiced in numerous cultures for many centuries. Devices for filtering exhaled smoke have also been introduced heretofore. One such early example was proposed by Martin, U.S. Pat. No. 5,353,814, entitled "Cigarette Smoke Cleansing and Smoking Device" and was awarded patent protection in 1994. Martin describes a smoking device where a traditional cigarette is smoked through a mouthpiece wherein the same mouthpiece is utilized to exhale therethrough for filtering exhaled smoke.

Importantly, in the last decade or so, traditional smoking of tobacco has been banned in places such as bars, casinos and beaches where smoking has traditionally been permitted. Smoking has additionally been banned on airline travel for at least about twenty years where no alternative has been adopted or provided. One drawback to the Martin device is that it will not completely eliminate smoke emitting from the device and any small smoke emission will be noticeable to people sensitive thereto, especially in an airline flight environment or similar enclosed space or building that's not well ventilated.

Also known heretofore are so called "electronic cigarettes" that typically use an electrical heating element to heat a liquid usually containing a mixture of nicotine and flavorings that produces a mist similar to smoke but without the excessive heat that causes combustion. Most electronic cigarettes, however, do not have complicated electronics and simply contain a battery electrically coupled to a heating element. A useful early example was proposed by Counts et al. U.S. Pat. No. 5,666,978 entitled "Electrical Smoking System for Delivering Flavors and Methods of Making Same" and was awarded patent protection in 1997. This particular prior art device has a receptacle for receiving tobacco or "tobacco flavored material" and electrical heating elements configured to the device for heating the material in order to emit vapors or aerosol for delivery to a smoker.

While these prior art devices are suitable in their idiosyncratic purposes, a need remains for an alternative to smoking cigarettes that further has exhale filter capability so that same is acceptable to somewhat sensitive environments such as airlines and enclosed places where children may be present.

One such viable improvement was proposed by present joint inventor, Shenkal, which comprises a diverter valve that provides an exhale filter function by diverting exhaled vapor about an outside of the device. Herein, the present continuation-in-part invention seeks to make alternative designs and improvements to this function. Accordingly as stated, U.S. patent application Ser. No. 14/121,917, entitled "Hybrid E-Cigarette/Vaporizer with Exhale Filter Capability," is incorporated herein by reference in its entirety.

Still further variations and improvements are disclosed herein. Initially, it is an object of the present invention to provide a unique shape for an electronic cigarette that user's may deem interesting and attractive, for holding in various ways creating a stylish smoking instrument. Still further, it is an object of the present invention to design an internal valve having a special structure and configuration. Yet further it is an object of the present invention to provide components that fit together in the manufacturing process that are interchangeable, modular and importantly fit concentrically about an elongated longitudinal axis.

Also further and in light of the above, it is an object of the present invention to provide an electronic smoking device that is a more versatile design and can additionally provide a smoking alternative in environments that have strict bans on smoking and vaping. More specifically, it is an object of the present invention to provide an inhale function and an exhale function. It is additionally an object of the present invention to provide a design comfortable to a user. Still further, it is an object of the present invention to provide a device that can be disassembled and modular to assist in the manufacturing process and to provide interchangeable like components. It is yet still further an object of the present invention to provide a design that includes a variety of innovative features over prior designs.

SUMMARY OF THE INVENTION

The present invention specifically addresses and alleviates the above mentioned deficiencies, more specifically, the present invention, in a first aspect, is an electronic cigarette and/or vaporizer comprising: a mouthpiece configured to a cooker chamber containing heated material; an after body portion configured to the cooker chamber wherein an electric heating element is provided to heat said heated material; a battery configured inside the after body portion providing current to the electric heating element; an igniter button for actuating said electric current; and a diverter valve for allowing air flow through the cooker chamber in an inhale function and for blocking air flow through the cooker chamber in an exhale function, further wherein the diverter valve transverses toward a first stop in the inhale function, and wherein the diverter valve transverses in an opposite direction toward a second stop in the exhale function.

The electronic cigarette in this aspect is additionally characterized wherein the diverter valve further comprises a duck bill valve configuration including a pair of flaps meeting at a ridge. The flaps extend to a cylindrical base which is supported by a disk at an end thereof. Alternatively, the diverter valve further has a dual duck valve configuration wherein a first pair of flaps meet at a center forming a ridge and wherein second and third pairs of flaps are on lateral sides of the first pair of flaps, wherein the first pair of flaps are open for the inhale function, wherein the first pair of flaps remain shut for the exhale function, wherein the second and third pairs of flaps are shut for the inhale function, and wherein the second and third pairs of flaps remain open for the exhale function.

The invention may be also characterized as follows: the mouthpiece together with the diverter valve, and further together with the cooker chamber, and further together with the after body portion are concentrically coupled about an elongated axis also along a column further wherein the mouthpiece and diverter valve and cooker chamber and after body portion are each integral modular components that may be interchanged with like components. Also alternatively, a plurality of exhale air vents around an outer periphery of a distal end of the after body portion are provided to the device. Alternatively, the vent holes could be at the ends.

The invention in this aspect is additionally characterized wherein the cooker chamber is configured to the after body portion via an igniter button portion, the igniter button portion comprising the igniter button. Further characterization includes wherein the mouthpiece is configured to the cooker chamber via an air plenum portion.

The invention in a second aspect is additionally characterized an electronic cigarette comprising: a mouthpiece configured to a cooker chamber containing heated material; an after body portion coupled to the cooker chamber wherein an electric heating element is provided to heat said heated material; a battery configured inside the after body portion providing current to the electric heating element; and a diverter valve for allowing air flow through the cooker chamber in an inhale function and for blocking air flow through the cooker chamber in an exhale function, further wherein the diverter valve includes left and right flaps that meet at a ridge, the ridge forming a point in a cross-section, wherein the diverter valve will open at the ridge when pressure decreases at an exterior thereof.

The invention in this aspect further includes an air plenum portion for holding inhaled vapor and diverting exhaled vapor around an outer portion of the cooker chamber, further wherein the mouthpiece is coupled to the cooker chamber via the air plenum portion therebetween, further wherein the mouthpiece together with the diverter valve, together with the air plenum portion, together with the cooker chamber, together with the after body portion are sequentially and concentrically coupled about an elongated axis, respectfully. Also further, the air plenum portion comprises a stop for preventing air from flowing around an outer portion of the cooker chamber in the inhale function.

Additionally the invention in this aspect, the cooker chamber comprises an inner cylinder for holding said heated material, further wherein the diverter valve rests against the inner cylinder during the exhale function thereby allowing air to divert around an outer portion of the cooker chamber in the exhale function.

The invention in this second aspect is additionally characterized wherein the after body portion comprising an elliptical shape in an after body portion cross-section, the elliptical shape having a major axis and a minor axis, the elliptical shape further tapering to a distal end of the electronic cigarette.

The invention is further characterized wherein the mouthpiece further comprising annular ribs for providing flexibility thereto, wherein further the mouthpiece is made from elastomer material providing flexibility. It is further contemplated that the cooker chamber comprises glass material providing transparency thereto.

In a third aspect, the invention is characterized as an electronic cigarette comprising: a mouthpiece configured to a cooker chamber containing heated material; an after body portion coupled to the cooker chamber; an electric heating element providing to heat said heated material; and an igniter button for actuating said heating element, the after body portion further comprising: an elongated and tapering shape; and a thicker mid-section to the electronic cigarette providing an oblique shape to the distal end. In still another similar aspect the shape is elliptical in the cross-section thereby allowing exhaled air to divert around an outer portion of the device. In still another similar aspect the shape of the after body portion comprises an elliptical shape in an after body portion cross-section, the elliptical shape having a major axis and a minor axis, the elliptical shape further tapering to a distal end of the electronic cigarette.

In still another aspect the invention is a vapor smoking device comprising: a mouth piece configured to a cooker chamber containing material to be heated; a body device coupled to a the cooker chamber wherein an electric heating element is provided to heat said heated material; a battery configured inside the body portion providing current to the electric heating element; and a filter assembly coupled to the body portion at a distal end thereof.

The invention in this aspect if further characterized in that the filter assembly further comprises: a fibrous corrugated paper filter; and a pair of felt filters configured on opposite sides of the corrugated paper filter, however with a charcoal granules filter also sandwiched therebetween. Also, the filter assembly includes a first and a second screen filter, the first screen filter adjacent to the first of the pair of felt filters, the second screen filter adjacent to a second of the pair of felt filters.

While the apparatus and method has or will be described for the sake of grammatical fluidity with functional explanations, it is to be expressly understood that the claims, unless expressly formulated under 35 USC .sctn.112, or similar applicable law, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC .sctn.112 are to be accorded full statutory equivalents under 35 USC .sctn.112, or similar applicable law. The invention can be better visualized by turning now to the following drawings wherein like elements are referenced by like numerals.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1B and FIG. 1C are side and top views of the preferred embodiment particularly showing a unique geometry and curvature of the device;

FIG. 4C is an isometric view of an alternative e-cigarette of the present invention;

FIG. 4D is a cross-sectional view thereof taken along line 4D-4D in FIG. 4C;

FIG. 4E is an enlarged view of a mouthpiece portion about line 4E in FIG. 4D;

FIG. 6A is an isometric view of yet another embodiment of the present invention;

FIG. 6B is an exploded view of a filter assembly of the present invention;

FIG. 6C is a cross-sectional view thereof taken along line 6C-6C in FIG. 6A; and FIG. 6D is an end view thereof.

DETAILED DESCRIPTION

Figure 1A:
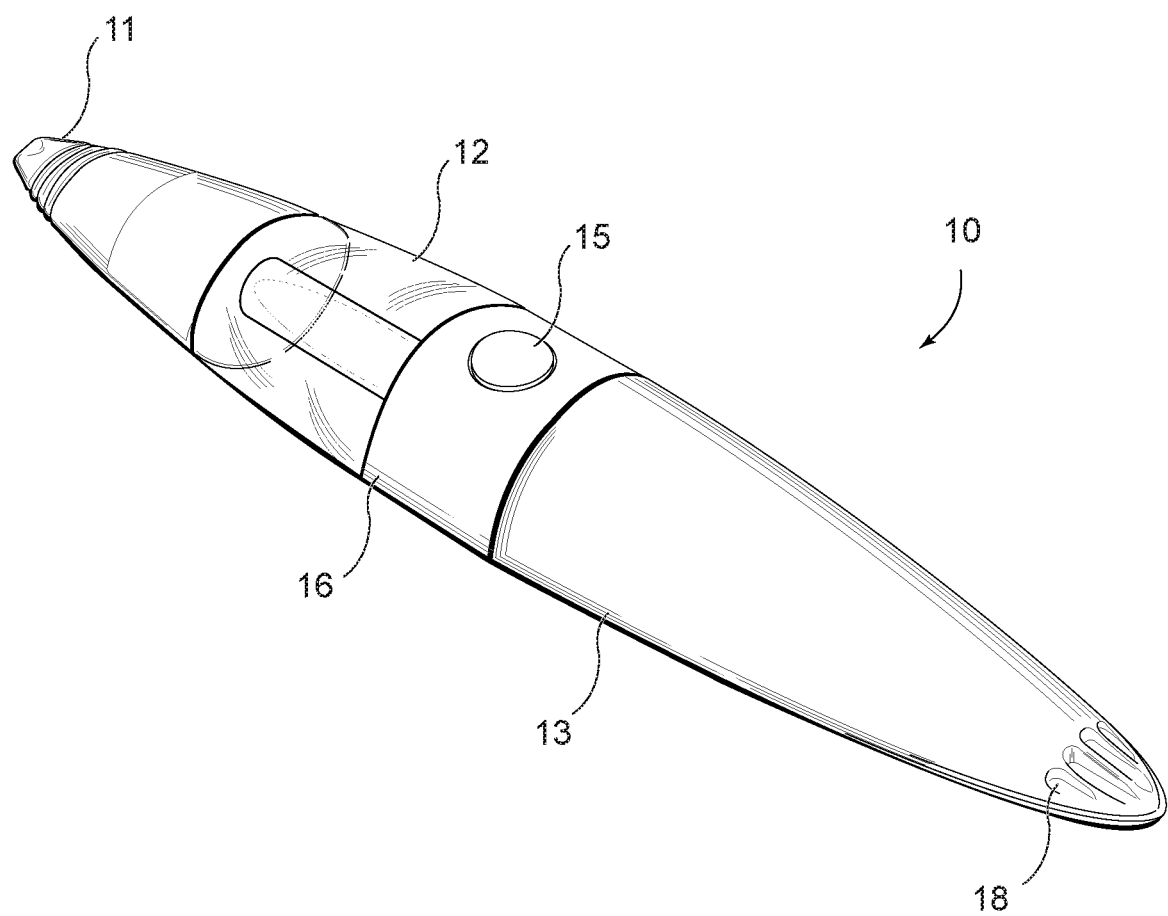
FIG. 1A is an isometric view of a first preferred electronic cigarette/vaporizer with exhale filter capability of the present invention.

Referring initially to FIG. 1A, a first preferred embodiment 10 is illustrated in an isometric view. Generally, mouthpiece 11 couples to cooker chamber 12 which couples to igniter button 15 portion 16, which in turn couples to after body portion 13. As shown, a cooker chamber 12 is made of transparent glass material providing an attractive appearance.

Importantly, the device 10 has a unique shape being an oblique alteration of a cigar shape more particularly shown in FIG. 1B and FIG. 1C. Specifically, the end sectional view (of after body portion (FIG. 3A)) will be elliptical or oval in shape and will have a thicker mid-section, then taper providing an oblique shape to the distal end. With specific attention to FIG. 1C, the device 10 is wider in the top aspect than in the side aspect (FIG. 1B). The wider lateral oval shape will allow for the exhale function to be channeled through outer portions of the device while the overall oblique tapering provides stylish handling and movements of the device in a user's hand. Additionally unique vent holes are provided to a distal end of the device.

Figure 3A:
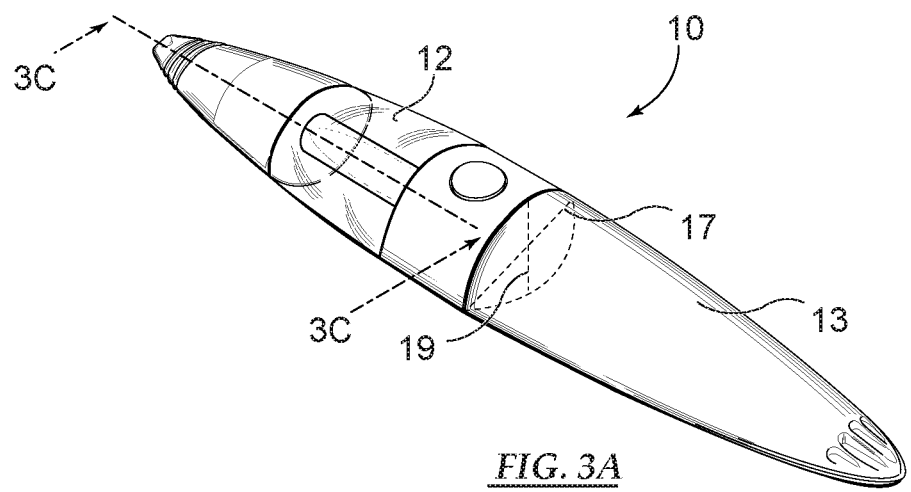
FIG. 3A is a more detailed isometric view of the first preferred embodiment.

Further with regard to FIG. 1B, FIG. 1C and FIG. 3A, the after body portion 13 has an elliptical shape 17 (together with 19) in an after body portion 13 cross-section, the elliptical shape having a major axis 17 and a minor axis 19, the elliptical shape further tapering to a distal end (toward vent holes 18) of the electronic cigarette 10. A clip may be provided as an optional accessory according to FIG. 1B.

Figure 2A:
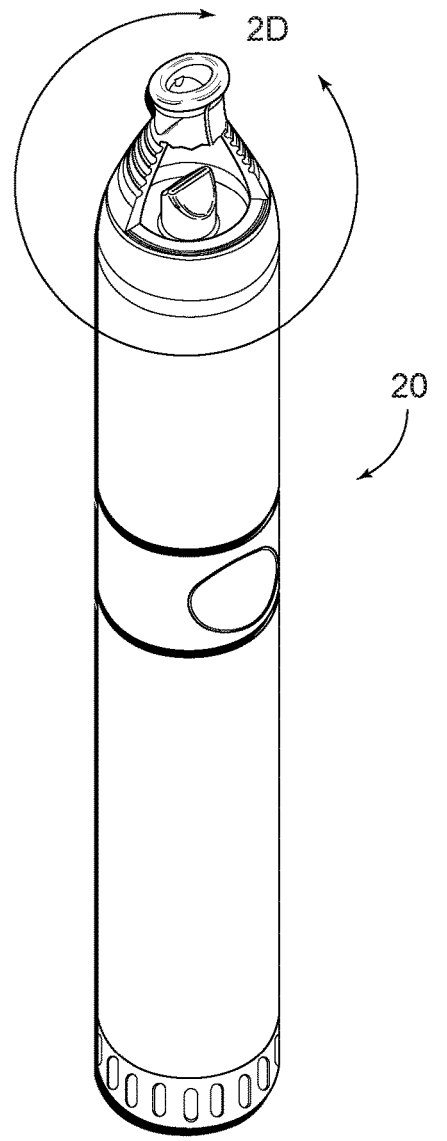
FIG. 2A is an isometric view of a second similar preferred embodiment having a more traditional cigar shape.
Figure 2B:
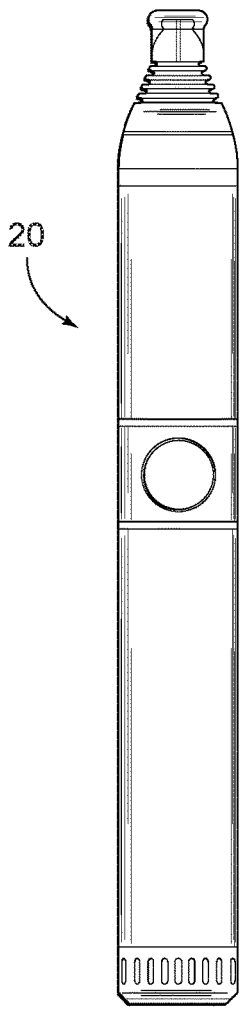
FIG. 2B is a top view of the device illustrated in FIG. 2A.
Figure 2C:
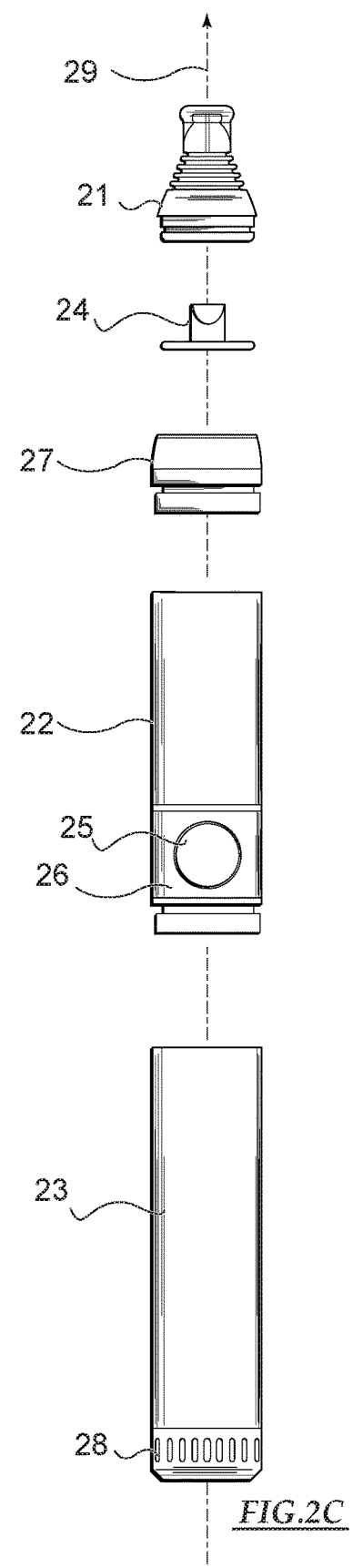
FIG. 2C is an exploded view thereof about its elongated axis.

FIG. 2A, FIG. 2B and FIG. 2C introduce a second embodiment 20 of the present invention. Specifically regarding FIG. 1A and FIG. 2C, the invention is characterized wherein the mouthpiece 11, 21 together with the diverter valve 24, and further together with the cooker chamber 12, 22 and further together with the after body portion 13, 23 are concentrically coupled about an elongated axis 29 also along a column 29, further wherein the mouthpiece 11, 21 and diverter valve 24 and cooker chamber 12 and after body portion 13 are each integral modular components that may be interchanged with like components. In other words, these components 21, 22, 23 24, are separately manufactured in then snuggly snap-fitted together also providing modularity. An example of like components is an after body portion 13, 23 of different colors, metallic in color or made of plastic or metal. Additionally, each of the first two embodiments 10, 20 include a plurality of exhale air vents 18, 28 around an outer periphery of a distal end of the after body portion 13, 23.

Figure 2D:
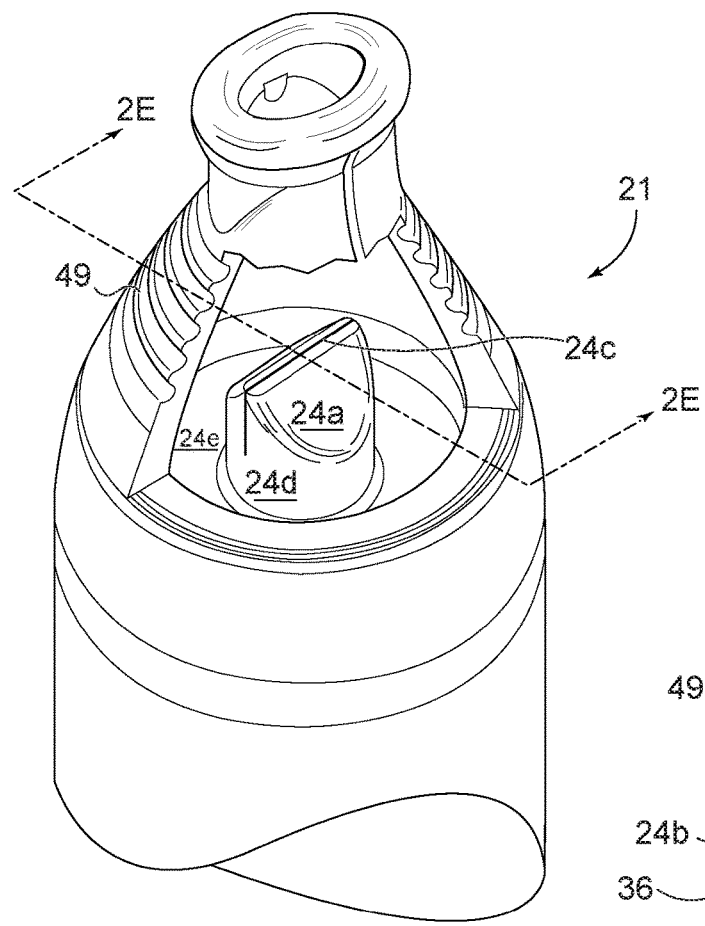
FIG. 2D is an enlarged view of a mouthpiece portion about line 2D in FIG. 2A.

FIG. 2D provides an enlarged view of a removable mouthpiece portion of the present invention. As stated, the mouthpiece is ribbed 49 for added flexibility and can be articulated more easily.

Figure 2E:
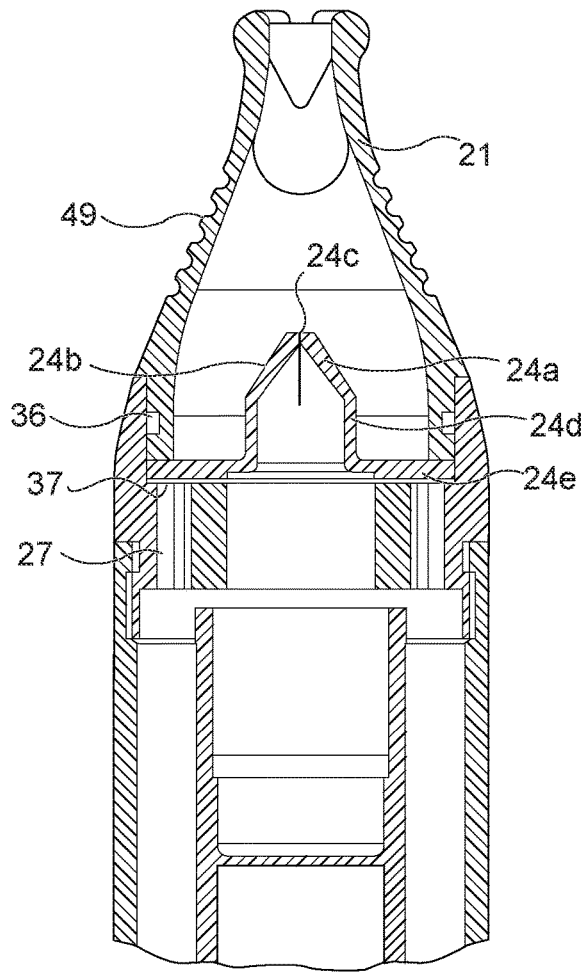
FIG. 2E is an sectional view taken along line 2E-2E in FIG. 2D.

Further regarding FIG. 2C and FIG. 2E, air plenum portion 27 is provided between the mouthpiece 21 and cooker chamber 22 for holding inhaled vapor and diverting exhaled vapor around an outer portion of the cooker chamber. Also further, components are aligned along an elongated axis 29. Specifically, the mouthpiece 21 together with the diverter valve 24, together with the air plenum portion 27, together with the cooker chamber 22, together with the after body portion 23 are sequentially and concentrically coupled about the elongated axis 29, respectively. The air plenum portion 27 has a stop 36 for preventing air from flowing around an outer portion of the cooker chamber 22 in the inhale function.

Further to the cooker chamber 12, 22 herein, an inner cylinder is provided for holding the heated material, as additionally detailed in the parent application. Regarding FIG. 3C, a first stop 36 halts transverse movement in the inhale function and forces air to come in the device 10 through the cooker chamber 12. Also with regard to FIG. 3D, the diverter valve 24 rests (as in stop 37) against the inner cylinder during the exhale function thereby allowing air to divert around an outer portion of the cooker chamber 12 in the exhale function.

Figure 3B:
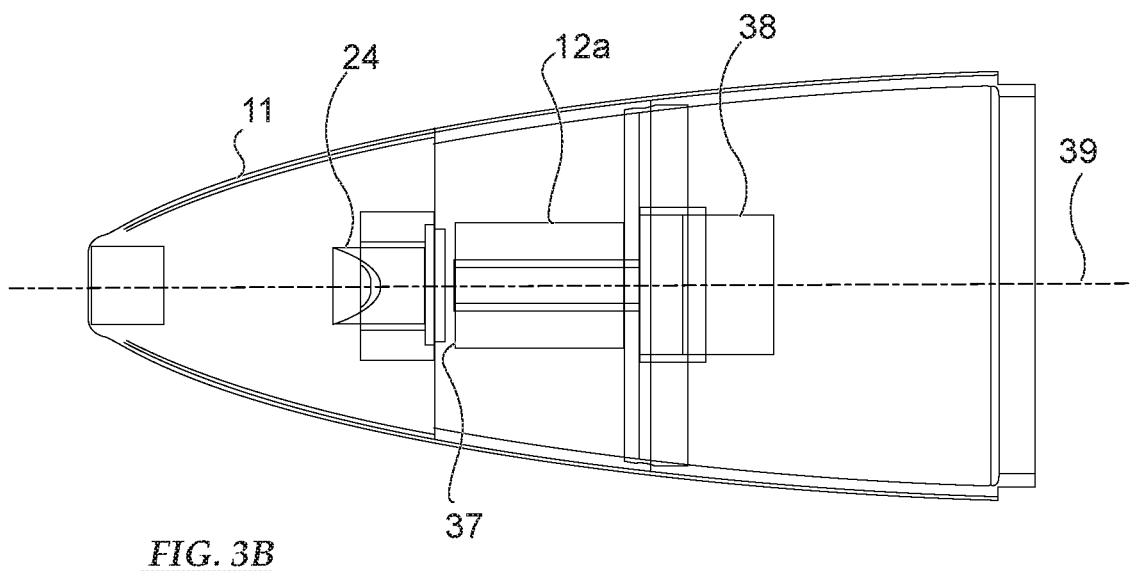
FIG. 3B is a profile view thereof revealing internal components.
Figure 3C:
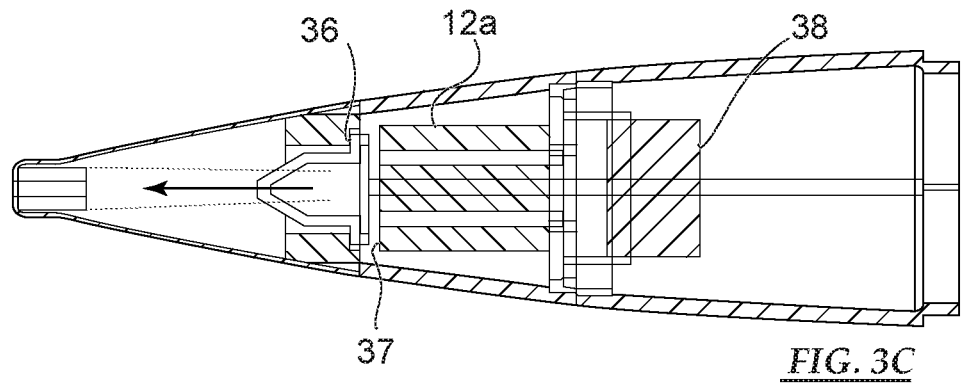
FIG. 3C and FIG. 3D illustrate cross-sectional views of the device taken along line 3C-3C in FIG. 3A, each illustrating inhale and exhale functions, respectively.
Figure 3D:
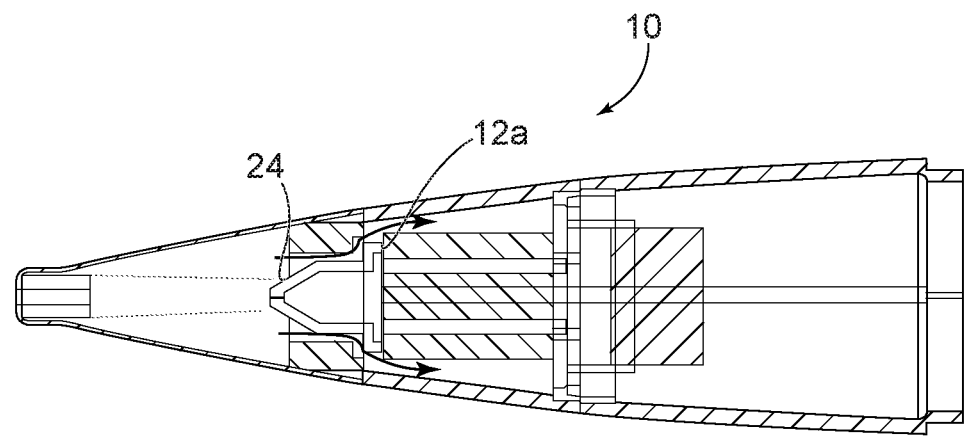

With regard to FIG. 3B, an additional side view of mouthpiece 11 and mid-section (cooker 12) revealing internal components is provided. FIG. 3C and FIG. 3D provide sectional views taken along line 3C-3C in FIG. 3A. The exemplary duckbill valve 24 is provided as detailed herein that is biased shut and requires a positive pressure in the interior thereof to open (or a negative pressure at the exterior as is caused by inhalation).

Further regarding FIG. 1A, FIG. 2E and FIG. 3C, first 10 and second 20 preferred embodiments are characterized as comprising: a mouthpiece 11, 21, 41 configured to a cooker chamber 12 containing heated material; an after body portion 13 coupled to the cooker chamber 12 wherein an electric heating element is provided to heat said heated material; and a battery configured inside the after body portion providing current to the electric heating element. Parent application incorporated by reference herein contains details regarding battery, heating element and cooker chamber. An igniter button 15 and igniter button portion 16 are provided for actuating the device 10, 20.

Also as shown in FIG. 2E, FIG. 3C and FIG. 3D, a diverter valve 24 is provided for allowing air flow through the cooker chamber in an inhale function. The diverter valve 24 further blocks air flow through the cooker chamber 12 in an exhale function by transversing toward a first stop 36 in the inhale function. Conversely, in the exhale function, the diverter valve 24 transverses in an opposite direction toward a second stop 37. In other words, the valve 24 moves directly back and forth, reciprocating between stops 36, 37.

With regard to FIG. 2D and FIG. 2E, the diverter valve 24 has a duck bill valve configuration and includes a pair of flaps 24a, 24b meeting at a ridge 24c. Additionally further, the flaps 24a, 24b extend downwardly to a cylindrical base 24d, wherein the cylindrical base 24d is further supported by a disk 24e at an end thereof. Also notably, the ridge 24c forms a point in a cross-section.

Figure 4A:
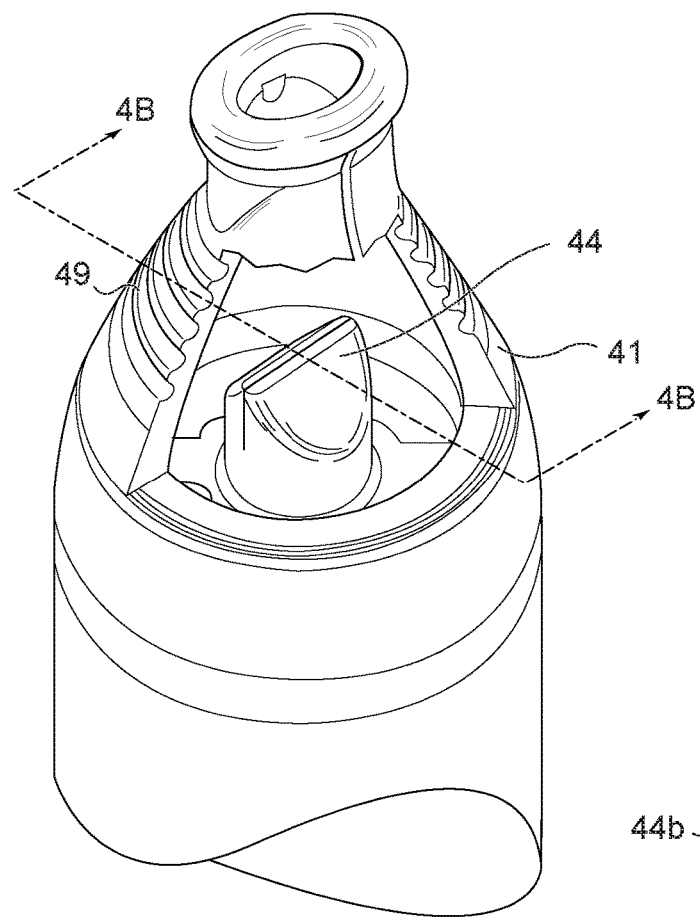
FIG. 4A is an isometric view of an alternative mouthpiece and diverter valve of the invention.

Regarding FIG. 2E and FIG. 4A, mouthpieces 21, 41 are provided with annular ribs 49 for providing flexibility thereto 21, 41. Also in a preferred embodiment, the mouthpiece 21, 41 is made from elastomer material providing flexibility. Mouthpiece 21, 41 is more specifically flexible comprising thermoplastic material providing enhanced feel and comfort. The ribbed portions 49 thereof allow for articulation and flexibility of the mouthpiece portion 21, 41.

Figure 4B:
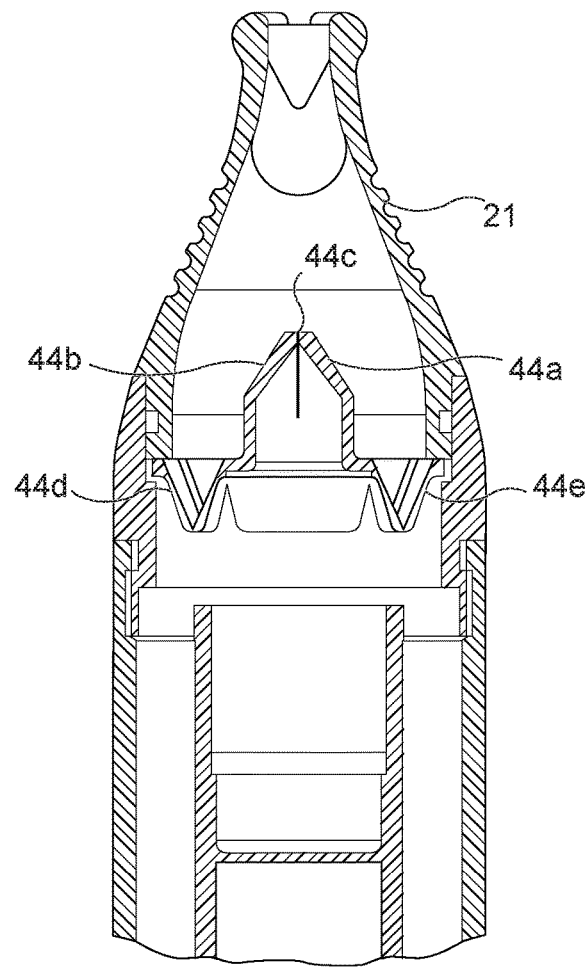
FIG. 4B is a cross-sectional view thereof taken along line 4B-4B in FIG. 4A.

With regard to FIG. 4B, a sectional view of a mouthpiece portion is shown with flaps 44d and 44e on lateral sides of diverter valve 44 that stay shut in the inhale function and will unseat and open in the exhale function. Importantly, FIG. 4B introduces a unique dual duckbill valve 44 assembly wherein in the valve remains shut to all air flow in the relaxed/steady state. Specially, the valve 44 is constructed so that only a one-way differential pressure will cause the valve 44 to open; and when pressure subsequently equalizes, the valve 44 returns to steady state. In the inhale function, pressure in one side will drop below pressure in the other side (center) 44c causing the valve 44 to open. In the exhale function, greater pressure in the one side will not cause the valve 44 to open in the center as its design acts like a check valve. Instead, air is diverted around the outside of the valve 44 into the device filter (located within after body portion 13). In other embodiments (FIG. 2A, FIG. 3B, etc.), the valve is just a single action valve 24 for the inhale function; and the exhale function will divert around the diverter valve 24 as detailed herein.

More specifically referencing FIG. 4B, the second diverter valve embodiment 41 is designed with a dual duck valve configuration wherein a first pair of flaps 44a, 44b meet at a center forming a ridge 44c and wherein second 44d and third 44e pairs of flaps are on lateral sides of the first pair of flaps 44a, 44b. As before, the center/first pair of flaps 44a, 44b are open for the inhale function; and, the first pair of flaps 44a, 44b are to remain shut for the exhale function. However, in this embodiment 41, the stops 36, 37 are not necessary and the valve 41 can remain stationary. Instead, the second 44d and third 44e pairs of flaps are shut for the inhale function, wherein the second and third pairs of flaps 44d, 44e remain open for the exhale function. More specifically, the flaps 44a, 44b, 44c, 44d are check valves that open when pressure drops at an exterior thereof (44a, 44b due to inhalation). Or, they 44c, 44d open when pressure at an interior thereof increases and reaches a threshold (due to exhalation). As shown in FIG. 4B, a slit is shown directly underneath ridge 44c between flaps 44a and 44b. It is additionally contemplated that the valve could operate without this additional slit.

Figure 4F:
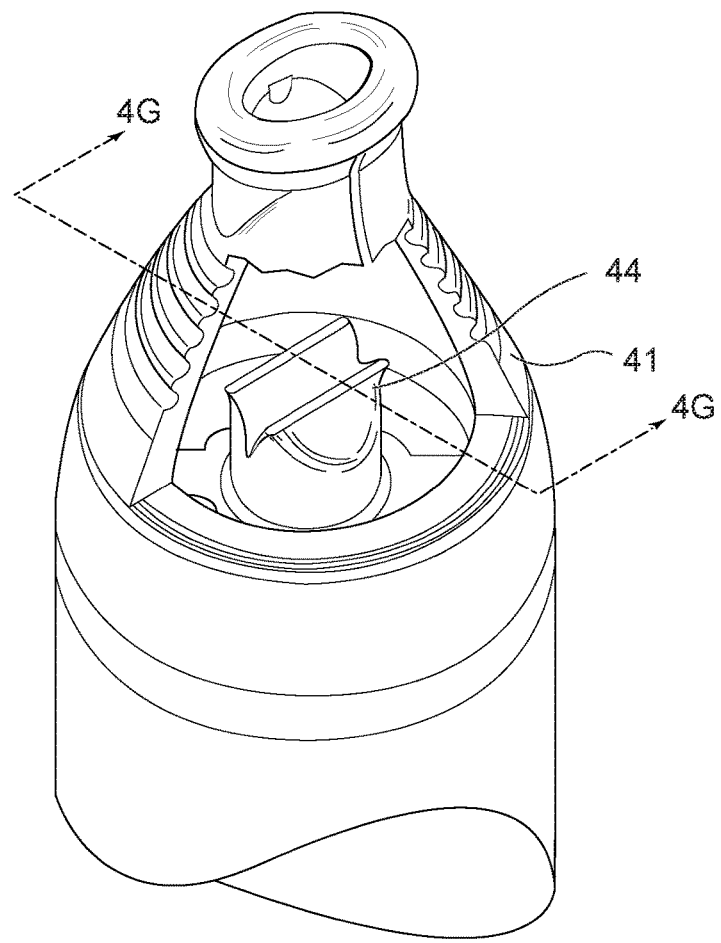
FIG. 4F is an alternative isometric view of the embodiment showing the diverter valve in an open inhale position.
Figure 4G:
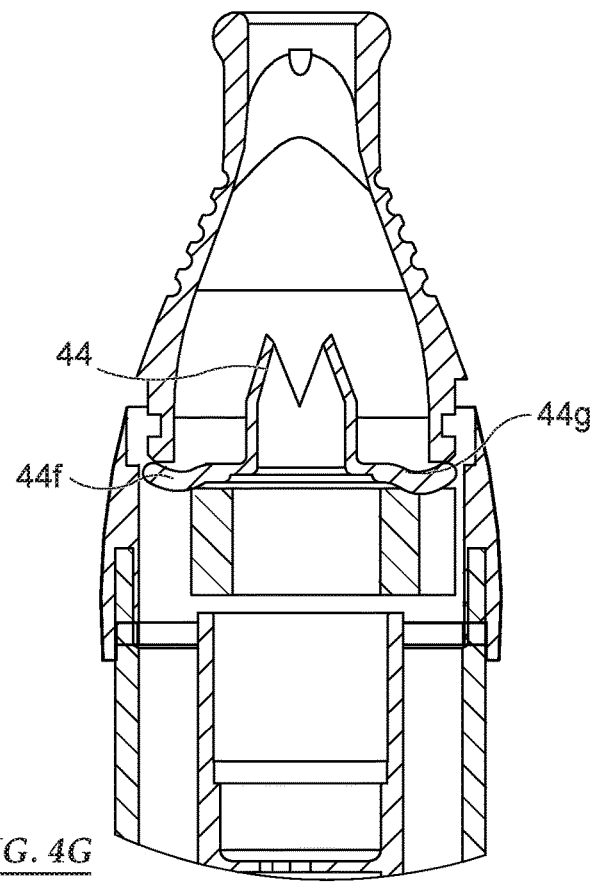
FIG. 4G is a cross-sectional view thereof taken along line 4G-4G in FIG. 4F.

With regard to FIG. 4E, slightly different structure for flaps 44f and 44g is shown however similar in nature where a flap 44a-g unseats due to differential pressure. Importantly FIG. 4F and FIG. 4G shows valve 44 and flaps 44a, 44b, 44c, 44f and 44g in their open and shut positions.

Further in other contemplated embodiments, the diverter valve for the inhale function could be a bellows type wherein the inhalation of air causes a bellows to expand and a valve to open. And further in the exhale function, the expanded bellows will vent back to its original state. In other embodiments, the valve is a membrane diaphragm that expands similar to the bellows. In all embodiments, the force of breath causes a force/differential pressure or a vibration or an expansion of a mechanical valve device.

An additional embodiment contemplated herein provides alternatives to include a star shaped duckbill valve 24.

Figure 5A:
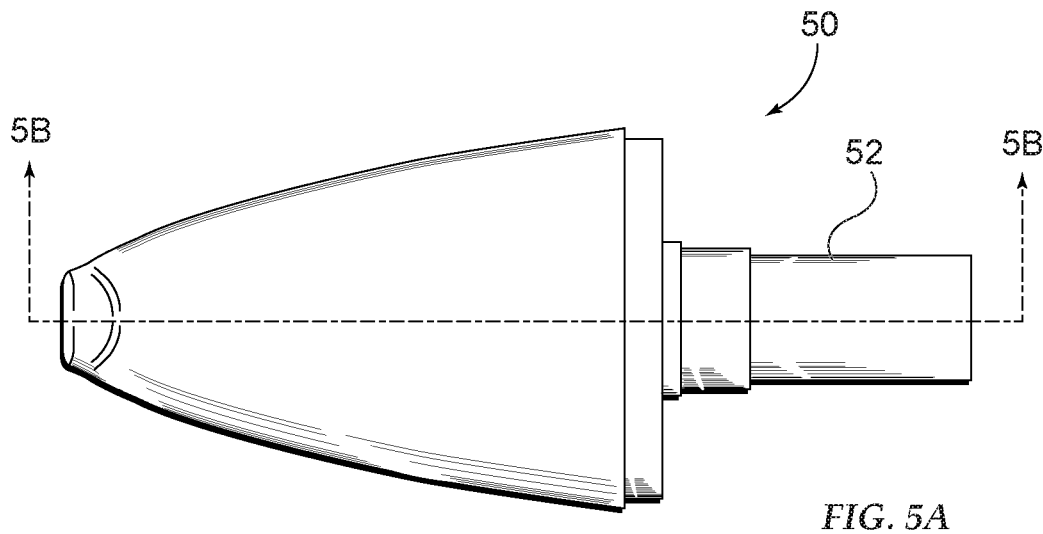
FIG. 5A is a profile view of yet another embodiment of the present invention.
Figure 5B:
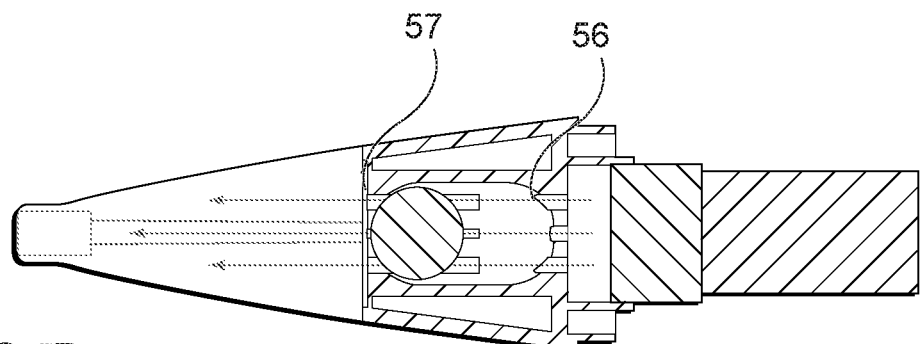
FIG. 5B is a cross-sectional view thereof taken along line 5B-5B in FIG. 5A, further illustrating an inhale function.
Figure 5C:
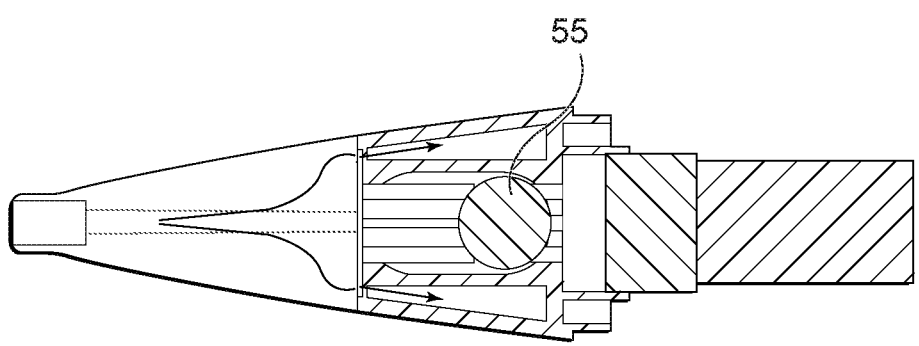
FIG. 5C is an additional cross-sectional view thereof showing an exhale function.

FIG. 5A, FIG. 5B and FIG. 5C illustrate yet another alternative valve concept 50 that could be configured to the present invention coupled to cooker chamber 52. Specifically, a ball 55 valve is normally seated (first stop 56) in the steady state position or in the exhale position. In the inhale position, the ball 55 valve unseats due to the differential pressure or the inhalation. The ball will then travel along its track until it is halted by a second stop 57; however air is still allowed to travel around the ball and stop 57. It should be noted that "ball" 55 is largely an equivalent of "disk" 24e since they both transverse back and forth to allow air either through the diverter valve 50 or around same.

With regard to FIG. 6A, a similar embodiment 70 is presented having a straight (and not oblique shape is provided in isometric view. Herein, mouthpiece 71 couples to inlet plenum 77 having diverter valve 74 that couples to cooker chamber 72 that couples to after body portion 73 that also has igniter button 75. Further herein, a filter assembly 60 is provided and should be appreciated that the filter assembly could be inside after body portion 73 and not a separate connecting component.

Referencing FIG. 6B, an exploded view of the filter assembly 60 is provided showing components 62, 63, 64, 65, normally housed therein. FIG. 6C is a cross-sectional view thereof taken along line 6C-6C in FIG. 6A. As shown, the filter assembly 60 has a fibrous corrugated paper filter 65 flanked by a charcoal granules/carbon pellets 64 filter and a first felt filter 63a. Also paper filter could be a heap filter paper, 100-200 microns, and alternatively polyester or polyether foam having various cell sizes, or it could be oiled or liquid.

Also with regard to FIG. 6B and FIG. 6C, a second felt filter 63b is provided adjacent to the charcoal granules 64 and this unit 63a, 63b, 64, 65 is flanked by first 62a and second 62b screen filters. Stated differently, the first screen filter 62a is adjacent to the first 63a of the pair of felt filters; and the second screen filter 62a is adjacent to the second 63a of the pair of felt. Screens 62a and 62b are more specifically disks having circular apertures. FIG. 6D is an end view illustrating filter assembly 60 having an additional grated end piece 61 where ultimately exhaled air is filtered and discharged as shown with arrows in FIG. 6C.

Last but not least, various examples of metallic, transparent and colored sections are contemplated, which could be modular in the manufacturing process as alluded to herein. An exemplary embodiment 10, 20 is 5½" long.

While the particular E-Cigarette with Valve Allowing Exhale Filter herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The invention claimed is:

1. An electronic cigarette assembly comprising:
   a mouthpiece;
   a cooking chamber operatively coupled to the mouthpiece and comprising an electric heating element;
   an after body portion operatively coupled to the cooking chamber for providing an electric current to the electric heating element; and
   a diverter valve configured to allow air flow from the cooking chamber to the mouthpiece and to inhibit air flow from the mouthpiece to the cooking chamber;
   wherein the diverter valve has a duck bill valve configuration comprising a pair of flaps configured to meet at a ridge;
   wherein each of the pair of flaps extends to an outwardly extending cylindrical base; and
   wherein the outwardly extending cylindrical base forms an additional flap.

2. The electronic cigarette assembly of claim 1, wherein the pair of flaps is configured to open when a user inhales air from the mouthpiece.

3. The electronic cigarette assembly of claim 1, wherein the additional flap is configured to open when a user blows emissions into the mouthpiece.

4. The electronic cigarette assembly of claim 1, wherein the mouthpiece, the diverter valve, the cooking chamber, and the after body portion are sequentially and concentrically coupled about an elongated axis.

5. An electronic cigarette assembly comprising:
   a mouthpiece;
   a cooking chamber operatively coupled to the mouthpiece and comprising an electric heating element;
   an after body portion operatively coupled to the cooking chamber for providing an electric current to the electric heating element;
   a filter assembly in selective communication with the mouthpiece; and
   a diverter valve;
   wherein the diverter valve is configured to
      allow air flow from the mouthpiece to the filter assembly; and
      inhibit air flow from the filter assembly to the mouthpiece;
   wherein the diverter valve has a duck bill valve configuration comprising a pair of flaps configured to meet at a ridge;
   wherein each of the pair of flaps extends to an outwardly extending cylindrical base;
   wherein the outwardly extending cylindrical base forms an additional flap; and
   wherein the mouthpiece, the cooking chamber, the after body portion, and the filter assembly are sequentially and concentrically coupled about an elongated axis.

6. The electronic cigarette assembly of claim 5, wherein the filter assembly comprises:
   a corrugated paper filter; and
   a pair of screen filters positioned on opposite sides of the corrugated paper filter.

7. The electronic cigarette assembly of claim 5, wherein the additional flap is configured to open to allow emissions blown into the mouthpiece to enter the filter assembly.

8. An electronic cigarette assembly comprising:
   a mouthpiece;
   a cooking chamber operatively coupled to the mouthpiece and comprising an electric heating element;
   an after body portion operatively coupled to the cooking chamber for providing an electric current to the electric heating element; and
   a diverter valve configured to allow air flow from the cooking chamber to the mouthpiece and to inhibit air flow from the mouthpiece to the cooking chamber;
   wherein the diverter valve has a dual duck bill valve configuration comprising
      a first pair of flaps configured to meet at a center ridge, and
      a second pair of flaps configured to meet at a lateral ridge on a lateral side of the first pair of flaps.

9. The electronic cigarette assembly of claim 8, wherein the first pair of flaps is configured to open when a user inhales air from the mouthpiece.

10. The electronic cigarette assembly of claim 8, wherein the first pair of flaps is configured to remain shut when a user exhales emissions into the mouthpiece.

11. The electronic cigarette assembly of claim 8, wherein the second pair of flaps is configured to open when a user exhales emissions into the mouthpiece.

12. The electronic cigarette assembly of claim 8, wherein the second pair of flaps is configured to remain shut when a user inhales air from the mouthpiece.

13. The electronic cigarette assembly of claim 8, wherein the dual duck bill valve configuration further comprises a third pair of flaps configured to meet at an additional lateral ridge on a lateral side of the first pair of flaps, opposite the second pair of flaps.

14. The electronic cigarette assembly of claim 13, wherein the second pair of flaps and the third pair of flaps are configured to open when a user exhales emissions into the mouthpiece.

15. The electronic cigarette assembly of claim 13, wherein the second pair of flaps and the third pair of flaps are configured to remain shut when a user inhales air from the mouthpiece.

16. The electronic cigarette assembly of claim 8, wherein the mouthpiece, the diverter valve, the cooking chamber, and the after body portion are sequentially and concentrically coupled about an elongated axis.

17. An electronic cigarette assembly comprising:
   a mouthpiece;
   a cooking chamber operatively coupled to the mouthpiece and comprising an electric heating element;
   an after body portion operatively coupled to the cooking chamber for providing an electric current to the electric heating element;
   a filter assembly in selective communication with the mouthpiece; and
   a diverter valve;
   wherein the diverter valve is configured to allow air flow from the mouthpiece to the filter assembly;
   wherein the diverter valve is further configured to inhibit air flow from the filter assembly to the mouthpiece;

wherein the diverter valve has a duck bill valve configuration comprising a pair of flaps configured to meet at a ridge;

wherein each of the pair of flaps extends to an outwardly extending cylindrical base; and wherein the outwardly extending cylindrical base forms an additional flap.

18. The electronic cigarette assembly of claim 17, wherein the additional flap is configured to open to allow emissions blown into the mouthpiece to enter the filter assembly.

19. The electronic cigarette assembly of claim 17, wherein the mouthpiece, the cooking chamber, the after body portion, and the filter assembly are sequentially and concentrically coupled about an elongated axis.

20. The electronic cigarette assembly of claim 19, wherein the diverter valve is concentrically coupled about the elongated axis between the mouthpiece and the cooking chamber.

21. An electronic cigarette assembly comprising:
a mouthpiece;
a cooking chamber operatively coupled to the mouthpiece and comprising an electric heating element;
an after body portion operatively coupled to the cooking chamber for providing an electric current to the electric heating element;
a filter assembly in selective communication with the mouthpiece; and
a diverter valve;
wherein the diverter valve is configured to allow air flow from the mouthpiece to the filter assembly;
wherein the diverter valve is further configured to inhibit air flow from the filter assembly to the mouthpiece;
wherein the diverter valve has a dual duck bill valve configuration comprising:
a first pair of flaps configured to meet at a center ridge, and
a second pair of flaps configured to meet at a lateral ridge on a lateral side of the first pair of flaps.

22. The electronic cigarette assembly of claim 21, wherein the second pair of flaps is configured to open to allow emissions blown into the mouthpiece to enter the filter assembly.

23. The electronic cigarette assembly of claim 21, wherein:
the dual duck bill valve configuration further comprises a third pair of flaps configured to meet at an additional lateral ridge on a lateral side of the first pair of flaps, opposite the second pair of flaps; and
the second pair of flaps and the third pair of flaps are configured to open to allow emissions blown into the mouthpiece to enter the filter assembly.

24. The electronic cigarette assembly of claim 21, wherein the mouthpiece, the cooking chamber, the after body portion, and the filter assembly are sequentially and concentrically coupled about an elongated axis.

25. The electronic cigarette assembly of claim 24, wherein the diverter valve is concentrically coupled about the elongated axis between the mouthpiece and the cooking chamber.

* * * * *